United States Patent [19]

Ginsberg et al.

[11] Patent Number: 4,666,891
[45] Date of Patent: May 19, 1987

[54] METHOD OF STIMULATING ANIMAL GROWTH BY ADMINISTERING FEED AND INOSINE COMPLEX

[75] Inventors: Theodore Ginsberg, Laguna Beach, Calif.; Miguel R. Lira, Coyoacan, Mexico

[73] Assignee: Newport AG, Zug, Switzerland

[21] Appl. No.: 679,914

[22] Filed: Dec. 10, 1984

[30] Foreign Application Priority Data

Feb. 8, 1984 [DE] Fed. Rep. of Germany ....... 3404315

[51] Int. Cl.$^4$ .............................................. A61K 31/70
[52] U.S. Cl. ..................................................... 514/45
[58] Field of Search ......................................... 514/45

[56] References Cited

U.S. PATENT DOCUMENTS 3,686,392  8/1972  Hamada et al. ........................ 514/47
3,728,450  4/1973  Gordon ................................. 514/45
3,857,940  12/1974  Gordon ................................. 514/45

FOREIGN PATENT DOCUMENTS 2462421  3/1981  France ................................... 514/45

Primary Examiner—Johnnie R. Brown
Assistant Examiner—Elli Peselev
Attorney, Agent, or Firm—Tarolli, Sundheim & Covell

[57] ABSTRACT

An animal additive for growth stimulation and lowering of feed consumption in accelerated fattening of domestic animals, has as an active agent a complex of inosine and an acid addition salt of dimethyl aminoisopropanol, or a mixture of these compounds. The compound or mixture may be used in the fattening of livestock, such as pigs, poultry, cattle, horses, sheep, dogs, and fish, and other animals. Particularly suitable is the complex of about 1 mole of inosine and about 3 moles of dimethyl aminoisopropanol.4-acetamino benzoate or the mixture of such ingredients in the indicated molar ratio.

15 Claims, No Drawings

METHOD OF STIMULATING ANIMAL GROWTH BY ADMINISTERING FEED AND INOSINE COMPLEX

FIELD OF THE INVENTION

This invention relates to growth stimulants for animals and to agents for increasing feed efficiency in animals. Also, the invention relates to a method of administering such agents to aid in the fattening of animals, and to a method of preparing a feed composition for animals useful in fattening thereof.

BACKGROUND OF THE INVENTION

In view of the continuously increasing need for inexpensive animal protein to feed the rapidly increasing population on earth, and also in view of the fact that the total amount of arable ground remains constant or even decreases, it is of great importance to be able to produce more meat from animals from a given amount of feedstuff. It is therefore necessary to improve the efficiency of the production of nutritious meat of pigs, poultry, cattle, horses, sheep, dogs and fish, by the use of growth promoting and feed efficiency agents as an additive to animal livestock feed. The term "livestock" will be used herein to refer to such animals grown for food.

Up to now, antibiotics with a narrow activity spectrum such as zinc bacitracin penicillin and streptomycin have been used on a large scale as growth stimulants. Antibiotics with a broad activity spectrum such as tetracycline, oxytetracycline and chloric tetracycline have also been so used. Usually such agents operate indirectly as growth promoters: first by slowing or even inhibiting the formation of certain germs in the gastrointestinal canal, thereby rendering usable for the production of meat that portion of the animal's feed intake otherwise necessary for keeping the germs alive; and second, by their preventive action against infectious diseases which would use a certain amount of energy.

The use of antibiotics as growth stimulants in animal feedstuff, however, may involve a certain amount of danger to human health. If such antibiotics are continuously given to animals in high doses, the meat from such animals may contain traces of the antibiotics, which could lead to development of a resistance to the antibiotic therapeutic effects in a person consuming such meat. The warnings of scientific authorities already have led to administrative restrictioms in using such agents as growth stimulants. Continuous use of antibiotics as growth stimulants in the feedstuff of animals and other livestock, that is, for non-therapeutic purposes, may be prohibited in the future.

Apart from such antibiotics, other kinds of compositions have been used as growth stimulants. Such ingredients include compounds with a pronounced antimicrobiological effect also used in human medicine, for instance furazolidone, also 3-(5-nitro-2-furfurylidenamino)-oxazolidone-(2), described for example in Jucker et al., Wiener Tierärztliche Monatszeitschrift, 1960, magazine 2/3. pages 100 to 103; or sulfanilamides. Furazolidone is described in Swiss Pat. No. 467,025. Furazolidone is $C_8H_7N_3O_5$, also N-(5-Nitro-2-furfurylidene-3-amino)-2-oxazolidone. Furazolidone, however, has the disadvantage of having a relatively pronounced toxicity. The prophylactic use of sulfanilamides has now been forbidden.

More recently, an increasing number of chemotherapeutic agents with an antimicrobiological effect have been used as growth stimulants to be added to the feedstuff of livestock. These have been specifically developed for this purpose. Some examples are: 2-(2-chinoxalinyl methylene) hydrazine carbonic acid methyl ester-N1,N4-dioxide, known under the generic name "carbadox", and olaquindoc 2'-hydroxyethylcarbamoyl)-3-methylchinoxalin-di-N-oxide. Both compounds, however, exhibit a certain degree of toxicity, and are also suspected as possibly being carcinogens.

It has recently been proposed to use a compound with the generic name "nitrovine" as a growth stimulant and additive to livestock feed. This compound may be described as 1,5-bis-(5-nitro-2-furyl)-1,4-pentadien-3-on-amidinhydrazonehydrochloride; see Swiss Pat. No. 460,501 as well as Schneider et al.. Landwirtschaftliche Forschung, 1970, volume XXIII, magazine 4, pages 350 to 352.

It is also common practice to use, as growth stimulants in feedstuffs, antibiotics which are not used in human medicine, such as virginiamycin. Such compounds usually develop their effect by suppressing the intestinal flora, thereby avoiding their feed-consuming metabolism. At the same time, they prevent diarrhea, salmonella, colienteritides and similar problems resulting from infectious diseases, which lowers effective feed utilization.

If these newly developed chemotherapeutics are administered during the entire rearing period of livestock or other animals, some precautions must be observed. The meat from such animals contains traces of such ingredients which are hygienically doubtful, and cross-resistances may be built up. Residues of antimicrobial inhibitors may cause technological problems in the microbiological treatment of animal products. See Eichhoff, MERCK-Kontakte 3/74, page 34. Also, in a manner similar to the action of pesticides, a concentration or build-up of such toxic substances in the human body is possible in certain organs. It is therefore advisable to use such compounds only in very small doses.

OBJECTS OF THE INVENTION

Consequently, it is a primary object of the invention to provide a growth stimulant and feed efficient agent which does not develop any direct chemotherapeutic effects, which is completely acceptable in regards to its toxicity and which especially does not leave any unnatural or unwanted residues in the meat.

It is a further object of the invention to provide an agent which stimulates the natural immune system, increases the immune reaction of the host cells, and thereby impedes the reproduction of virus protection.

It is a still further object of this invention to provide an agent which meets these requirements and which is at the same time commercially acceptable.

It is a still further object of this invention to provide an agent suitable for promoting growth and lowering feed consumption in livestock.

Finally it is an object of the invention to provide a method of administering such agents to aid in the fattening of animals and, further, to provide a method of preparing a feed composition useful in fattening of animals.

SUMMARY OF THE INVENTION

In accordance with the present invention, it has been found that a complex of inosine and an acid addition salt of dimethyl aminoisopropanol, or a mixture of these ingredients, shows the desired growth promoting effect in fattening livestock or other animals, without having the disadvantage of secondary physiological effects. Complexes of inosine and acid addition salts of dimethyl aminoisopropanol, particularly consisting of inosine and dimethyl aminoisopropanol.4-acetamino benzoate are well known in the art. Inosine is 6-hydroxypurin-9D-ribofuranoside, or hypoxanthineriboside. Such compounds are described as nonspecific ingredients having a broad effective impact on different DNS- and RNS-viruses, as compositions for improving learning capability, and as hardening agents for melamine and urea formaldehyde resins. On examining a number of virus diseases it has been found that such inosine complexes do not have a direct chemotherapeutic effect.

It has furthermore been found that feeding livestock with a feedstuff containing the inosine complex compound or mixture results in a weight gain of about 10 percent above average after only a few weeks of fattening.

The growth promoting and feed efficiency effect of the inosine complex disclosed herein is not limited to certain kinds of animals. Comparative fattening tests have been performed with newly born plglets, pigs weighing about 90 lbs., with young chickens, young turkeys, calves, young horses, lambs, young dogs, carp, and trout. In addition to the normal feed, a complex of inosine and dimethyl aminoisopropanol.-acetamino benzoate was administered. In all cases a higher weight gain was observed than with animals of a comparative group that received the same amount of feed together with a placebo. The same results were achieved when a mixture of inosine and dimethyl aminoisopropanol.4-acetamino benzoate was used instead of the complex compound, proviided that the mixture contained both components in a sufficient quantity.

During such fattening tests it was possible to stop the use of antibiotics. The animals nevertheless enjoyed excellent health during the full period of administration of the inosine complex, even if the hygienic conditions were only average and sterile conditions were not observed. The test animals which received the inosine complex usually were much more lively than and showed an increased vitality compared to the control group.

DESCRIPTION OF PREFERRED EMBODIMENTS

The present invention is directed to a feedstuff additive suitable for growth stimulation and feed efficiency during the accelerated fattening of livestock. The essential ingredient is a complex of inosine and an acid addition salt of dimethyl aminoisopropanol, or a mixture of these ingredients.

Any acid forming compatible salts are basically usable as acids for forming the addition salts of dimethyl aminoisopropanol, such as hydrochloric acid, phosphoric acid, acetyl salicylic acid, 4-amino benzoic acid, sulfuric acid, tartaric acid, fumaric acid, succinic acid, citric acid, salicylic acid, adipic acid, methane sulfonic acid, p-amino succinic acid and 4-acethylamino benzoic acid, the latter one being most preferred. The complex compound consisting of inosine and dimethyl aminoisopropanol.4-acetamino benzoate is preferred, especially since it is physiologically compatible and has proved to be more stable in the presence of moisture than the complex salts of the other acids. Preferably, a complex of 1 mole inosine and 3 moles dimethyl aminoisopropanol.4-acetamino benzoate is used, or a mixture consisting of such components with the same molar ratio.

The present invention is also directed to a method of using the aforementioned complex of inosine and an acid addition salt of dimethyl aminoisopropanol or of the aforementioned mixture of such ingredients, as a growth stimulant and as a feed efficiency agent in the fattening of animals and other livestock, such as pigs, poultry, cattle, horses, sheep and all kinds of fish. The agent is preferably used in the form of a complex compound consisting of inosine (1 mole) and dimethyl aminoisopropanol. -4-acetamino benzoate (3 moles).

The present invention finally is also directed to the preparation of a feed composition for animals. Such composition may be prepared as follows:

A first intermediate product is prepared by reacting inosine with 1 to 10 molequivalents of a dialkylamino alkanol or of an addition salt of a physiologically acceptable acid of dialkylamino alkanole responding to the formula

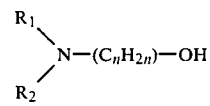

which $R_1$ and $R_2$ each represent a low alkyl group and n is an integer between and including 2 and 4. This first intermediate product, which is in the form of a complex compound, is then transformed into the salt of a physiologically acceptable acid to obtain a second intermediate product, namely the ingredient as hereinbefore mentioned. Finally this second intermediate product is mixed with a desired conventional animal feed product to obtain said feed composition.

The compositions of the present invention are suitable for the fattetning of pigs, particularly newly born piglets, but also for accelerated fattening of older or partly grown pigs. The same agent may also be successfully used as a growth stimulant for fattening young chickens, broilers, turkeys, ducks and geese, etc. The inosine complex according to the present invention can also be used as a growth stimulation and feed efficiency agent for calves and cattle. Good results have been obtained by using this agent for the accelerated fattening of lambs Finally, the composition described herein may be used to reduce feed usage in the rearing of fish such as carp, trout, whitefish, pike, perch, grassfish, catfish, eels, etc. in ponds or pools and in so-called aqua-cultures.

In most of these cases, but depending on the purpose, the growth stimulant is administered orally to the animal. In selecting the individual administration form, the specific characteristics of each species, as well as the age of the animals, must be taken into account. It must furthermore be made certain in practice that each animal actually receives its specific dosage of the agent and that no avoidable losses occur because of spoiling or spilling. In cases in which young animals are still fed by their mother, the agent is preferably injected directly into the throat in the form of an aqueous solution. For calves the agent may be administered in the form of a milk solution. Administration in the drinking water is possible as well. For animals which already consume solid feed, the agent may be mixed with the feed. An especially preferred kind of administration is in the form of pellets or cubes which contain, besides the growth promoting agent, also those feed components especially preferred by the animal in question, like molasses, fat, vegetable and animal proteins (soy bean sprouts. corn sprouts, yeast powder, whey, casein, sea-weed powder, fish powder, etc.), along with vitamins, salt and trace elements.

The composition may be administered to fish in the form of capsules with a diameter of 1 to 7 mm which are insoluble in water at room temperature. Another possibility is administration in fat-containing food pellets whereby the agent is insoluble or almost insoluble in water.

Dosage requirements

The growth stimulant generally consists of a complex compound of 1 mole of inosine and 3 moles of dimethyl aminoisopropanol-4-acetamino benzoate. If the complex forming ingredient for the inosine is an acid addition salt of a different acid, the dosage must be va ied in accordance with the change of the total molecular weight.

It should be noted that the effective amount of the growth stimulant, and the dosage, will depend on the specific species, the age of the animal and the method of rearing.

It will be seen that the term "effective amount" has a wide range and varies according to the needs of the animals, the goals desired from use of the agent, and other factors. Examples and further description will make this clear.

It is usually advisable to star the administration of the growth stimulant shortly after birth in order to stimulate the immuno-reaction-system of the animal at the beginning of its growth. During the first weeks, piglets are daily given about 60 to 80 mg of the agent per animal. The dosage during the first 6 weeks is usually kept in the range of 40 to 80 mg per kg of body weight. The agent or ingredient of the present invention is administered to young chickens in the form of pellets, with the amount of the agent in the range of 20 to 100 mg per kg of the total feed weight, excepting drinking water. Broilers are fed approximately 50 to 500 mg of the agent per kg of the total feed weight.

Calves still being nourished by their mothers initially need only a relatively small amount of the agent, as they are receiving immunizing agents together with the mother's milk. Consequently, only about 1 to 10 mg of the agent are administered on 5 out of 7 days during this period. Calves being fed with artificial milk containing all necessary food components receive the agent together with that milk, in dosage of about 50 to 100 mg per kg of body weight per day. Calves and young oxen should be given the agent of the present invention with the concentrated feed in a daily dosage of about 100 to 1000 mg per kg body weight. The agent is added to the concentrated feed in the form of a premix made from soy flour, containing 20 to 50% of the agent. The manner of administration and the dosage for foals, lambs and puppies, who are usually nourished by their mothers, is similar to that for suckling calves.

Fish are generally given about 50 to 100 mg of the agent per kg of feed as soon as they are able to eat solid feed. From the age of 3 months up to 1 year, fish are given 100 to 1000 mg of the agent per kg of feed.

EXAMPLES

Example 1

Two groups of 5 litters of eight, five-day-old piglets each, were treated. One group received a growth stimulant consisting of 1 mole inosine and 3 moles dimethyl aminoisopropanol.4-acetamino benzoate. The other group received the same quantity of a placebo (water and 2 percent sodium chloride). Both additives were in addition to the normal feed. The dosage was 50 mg per kg body weight dissolved in 25 ml of water, and the solution was administered directly into the throat.

After six weeks the litters which received the growth stimulant showed weight gain of 2.5 to 3 kg compared with the litters of the other group. The gain in weight was approximately 10% above the average.

Example 2

Comparison test of pig fattening

A group of 20 pigs with a weight of approximately 40 kg each was fattened in single boxes with a basic feedstuff composed as follows:
- 16% raw protein
- 14% digestible raw protein
- 5% raw fibers
- 63.3% starch units
- 0.7% lysine
- 1.0% premix (50% growth stimulant consisting of 1 mole inosine and 3 moles dimethyl aminoisopropanol.4-acetamino benzoate and 50% soy flour)
- 1.0% placebo (100% soy flour).

After 53 days the animals were weighted. The animals treated with the growth stimulant according to the presen invention showed an average weight gain of 9.5% more than the non-treated animals.

Example 3

Fattening of chickens

Five hundred (500) ppm of an agent consisting of 1 mole inosine and 3 moles dimethyl aminoisopropanol.4-acetamino benzoate were added to the feed for chickens. The following results were obtained, after a fattening period of 50 days:

Young chickens: Weight gain was 5 to 7% above the average. Improvement of the utilization of the feed (kg in feed/kg weight gain) was +4.5%.

Broilers: Weight gain was 12 to 15% above the average. Improvement in the utilization of the feed was +12 to +13%.

Example 4

Comparison test - fattening of calves

Twenty weaned calves were fed an artificial milk containing all the necessary nutritive ingredients, in the usual dosage. Half of the calves also received a growth stimulant consisting of 1 mole inosine and 3 moles dimethyl aminoisopropanol.4-acetamino benzoate. The stimulant was given in a dose of 6 g dissolved in the milk for each animal during 6 out of 7 days. After 50 days the animals were weighted. The animals treated with the growth stimulant showed an average weight gain of 7.3% more than the nontreated animals.

Example 5

Comparison test - fattening of oxen

Twenty-four oxen with an average basic weight of 100 kg were divided into two groups. All animals received the same concentrated feed containing all necessary additives and trace elements as well as bruised corn, corn-cob sprout and hay. Each of 12 animals furthermore received 550 ppm of an agent consisting of 1 mole inosine and 3 moles dimethyl aminoisopropanol-4-acetamino benzoate. After 105 days the weight gain of the treated animals was significantly higher by 8% than that of the control animals.

Example 6

Fattening of lambs

A number of lambs were given concentrated feed, containing a sufficient quantity of trace elements and also hay. One half of the animals were additionally given a growth stimulant consisting of 1 mole inosine and 3 moles dimethyl aminoisopropanol-4-acetamino benzoate in a dose of 1000 ppm. The weight gain of the treated animals was 10% higher than that of the control animals.

Example 7

Fattening of fish

Carp were fattened with normal pellelized feed which also contained 1000 ppm growth stimulant consisting of 1 mole inosine and 3 moles dimethyl aminoiso-propanol.4-acetamino benzoate. This process resulted in a significantly higher weight gain as compared with normally fed carps. Similar effects were observed in fattening trouts. In this connection it is remarkable that the death rate among fish fed with the agent was considerably lower than in those given the normal feed.

GENERAL REMARKS

The preferred composition for the growth stimulant of the present invention is a complex or mixture of inosine and dimethyl aminoisopropanol.4-acetamino benzoate. This invention provides a feed additive composition which is safer than those of the prior art, even in high doses. Inosine (6-hydroxypurin-9D-ribofuranoside, or hypoxanthineriboside) is a natural component of meat and is also found in yeasts, beet sugar and other food products. Inosine activates the functions of cells. 4-amino benzoic acid is identical with the growth agent H which has been isolated from yeasts and is integrated, for instance by bacteria into folic acid, which is of vital importance for the growth of single cell animals such as microbes. 4-amino benzoic acid is removed from the tissues of vertebrates mainly in the form of 4-acetamino benzoic acid. It is therefore evident that dimethyl aminoisopropanol-4-acetamino benzoate is extremely well compatible and is furthermore quickly removed from the tissues of vertebrates. As a consequence, the existence of residues originating from said agent and not naturally being found in the tissues of livestock, has never been proved to exist.

For this reason, the inosine complex according to the present invention is much superior in terms of compatibility than other known growth stimulants. For the same reasons, meat produced using the growth stimulants disclosed herein can be safely consumed by humans. The growth stimulants of the present invention are also demonstrably safer than other known stimulants.

What we claim is:

1. A method of stimulating animal growth which comprises administering to said animal a combination of animal feed and an effective amount of a growth stimulating agent selected from the group consisting of (i) a complex of inosine and an acid addition salt of dimethyl aminoisopropanol and (ii) a mixture of inosine and an acid addition salt of dimethyl aminoisopropanol.

2. A method as defined in claim 1 wherein said acid addition salt of dimethyl isopropanol comprises dimethyl aminoisopropanol.4-acetamino benzoate.

3. A method as defined in claim 2, wherein said growth stimulating agent comprises about one part by molar weight of inosine and about ten parts by molar weight of dimethyl aminoisopropanol.4-acetamino benzoate.

4. A method as defined in claim 2, wherein said growth stimulating agent comprises about one part by molar weight of inosine and about four parts by molar weight of dimethyl aminoisopropanol.4-acetamino benzoate.

5. A method as defined in claim 2, wherein said growth stimulating agent comprises about one part by molar weight of inosine and about three parts by molar weight of dimethyl aminoisopropanol.4-acetamino benzoate.

6. A method as defined in one of claims 1 or 2 wherein said animal is an animal selected from the group consisting of pigs, poultry, cattle, sheep. dogs, and fish.

7. A method as defined in claim 2, further comprising the step of mixing said growth stimulating agent with animal feed prior to administering said agent to said animal.

8. A method as defined in claim 7, wherein said animal is a piglet and wherein said growth stimulating agent is admixed to said animal feed in a dose of 40 to 80 mg per kg body weight of the animal.

9. A method as defined in claim 8, wherein said dose is 50 mg per kg body weight of the animal, said agent being dissolved in 25 ml of water.

10. A method as defined in claim 7, wherein said animal is a pig and wherein said growth stimulating agent is admixed to said animal feed in a dose of 50 to 500 mg agent per kg of the feed.

11. A method as defined in claim 7, wherein said animal is a chicken and wherein said growth stimulating agent is admixed to said animal feed in a dose of 20 to 100 mg agent per kg of the feed.

12. A method as defined in claim 7, wherein said animal is a calf and wherein said growth stimulating agent is admixed to said animal feed in a dose of between 1 to 10 g per calf on 6 out of 7 days, preferably about 6 g.

13. A method as defined in claim 7, wherein said animal is a ox and wherein said growth stimulating agent is admixed to said animal feed in a dose of 100 to 1000 mg agent per kg of body weight of the animal.

14. A method as defined in claim 7, wherein said animal is a lamb and wherein said growth stimulating agent is admixed to said animal feed in a dose of 50 to 200 mg agent, preferably 100 mg agent per kg of the feed.

15. A method as defined in claim 7, wherein said animal is a fish and wherein said growth stimulating agent is admixed to said animal feed in a dose of 50 to 1000 mg agent per kg of the feed, in a dose of 50 to 500 mg agent per kg of the feed for young fish up to an age of 3 months, and in a dose of 100 to 1000 mg agent per kg of the feed for fish of an age between 3 months and 1 year.

* * * * *